United States Patent

Shemano

[11] 3,947,593
[45] Mar. 30, 1976

[54] PHARMACEUTICALLY USEFUL BIS-AMINE DERIVATIVES

[75] Inventor: Irving Shemano, Cincinnati, Ohio

[73] Assignee: Richardson-Merrell Inc., Wilton, Conn.

[22] Filed: June 15, 1973

[21] Appl. No.: 370,290

[52] U.S. Cl. .............................. 424/330; 424/274
[51] Int. Cl.² .................................. A61K 31/135
[58] Field of Search .................................. 424/330

Primary Examiner—Jerome D. Goldberg
Attorney, Agent, or Firm—L. Ruth Hattan; Eugene O. Retter; George W. Rauchfuss, Jr.

[57] ABSTRACT

Compounds of the following general structure are useful in treating conditions of delayed hypersensitivity:

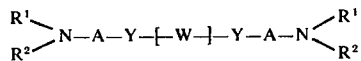

wherein [W] represents an aromatic polycyclic nucleus selected from fluoranthene, fluorene, fluoren-9-ol, fluoren-9-one, carbazole, N-(lower) alkyl carbazole or anthraquinone; Y represents carbonyl, divalent sulfur or oxygen; with the proviso that when Y is carbonyl, [W] is other than fluoren-9-ol or anthraquinone; A represents a straight or branched alkylene chain of from 1 to 6 carbon atoms; and each of $R^1$ and $R^2$ represents hydrogen, lower alkyl of from 1 to 4 carbon atoms, or alkenyl of from 3 to 6 carbon atoms having the vinyl unsaturation in other than the 1-position; and pharmaceutically useful acid addition salts thereof.

13 Claims, No Drawings

PHARMACEUTICALLY USEFUL BIS-AMINE DERIVATIVES

FIELD OF INVENTION

This invention relates to the use of bis-amine derivatives in the treatment of conditions of delayed hypersentitivity.

DESCRIPTION OF PRIOR ART

Bis-amine derivatives of fluoranthene are described in U.S. Pat. No. 3,707,471 and Great Britain patent 1,304,651. Bis-amine derivatives of fluorene and fluoren-9-one are described in U.S. Pat. Nos. 3,592,819, 3,692,907 and Great Britain patent 1,286,755. Bis-amine derivatives of fluoren-9-ol are described in U.S. Pat. Nos. 3,592,819 and 3,692,907. Bis-amine derivatives of anthraquinone are described in Belgian patent 767,210, which is equivalent to pending U.S. application Ser. No. 37,312. Each of these disclosures describes the compounds therein as being useful as antiviral agents and do not suggest or render obvious the use of the compounds disclosed herein in the treatment of conditions of delayed hypersensitivity.

SUMMARY OF INVENTION

Compounds of the following general Formula I are useful in treating conditions of delayed hypersensitivity:

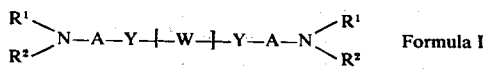

Formula I wherein [W] is an aromatic polycyclic nucleus selected from fluoranthene, fluorene, fluoren-9-ol, fluoren-9-one, carbazole, N-(lower)alkylcarbazole, or anthraquinone; Y is selected from carbonyl, oxygen or divalent sulfur with the proviso that when Y is carbonyl, [W] is other than fluoren-9-ol or anthraquinone; A is a straight or branched alkylene chain of from 1 to 6 carbon atoms; and each of $R^1$ and $R^2$ is selected from hydrogen, straight or branched lower alkyl of from 1 to 4 carbon atoms, or alkenyl of 3 to 6 carbon atoms having the vinyl unsaturation in other than the 1-position. Pharmaceutically acceptable acid addition salts of the compounds of general Formula I are within the scope of this invention.

DETAILED DESCRIPTION OF INVENTION

The compounds of general Formula I are bis-amine derivatives fluoranthene, fluorene, fluoren-9-ol, fluoren-9-one, carbazole, N-(lower)alkyl carbazole and anthraquinone as represented by the following respective general Formulas II to VII.

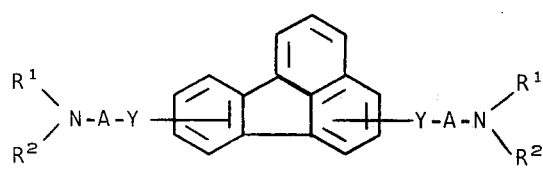

Formula II

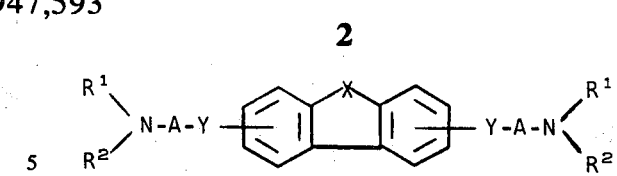

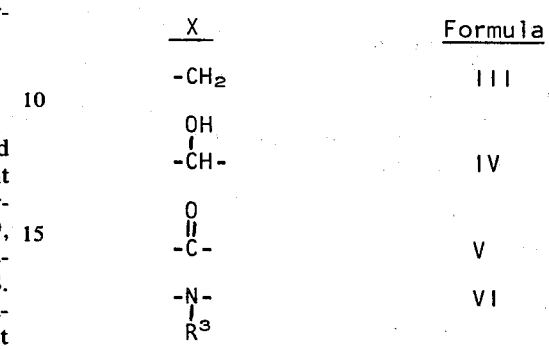

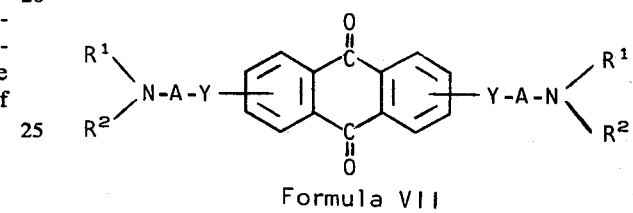

Formula VII

In the above general Formula II to VII, Y represents carbonyl, oxygen, or divalent sulfur except that in Formulas IV and VII, Y is other than carbonyl; A, $R^1$ and $R^2$ have the meanings defined in general Formula I. In Formula VI, $R^3$ represents hydrogen or lower alkyl of 1 to 4 carbon atoms such as, methyl, ethyl, n-propyl or n-butyl.

In the compounds of general Formula II one of the basic substituent groups as represented by

is attached to any one of the carbon atoms of the naphthalene portion of the tetracyclic nucleus and the other such basic substituent is attached to any one of the carbon atoms of the benzenoid ring of the tetracyclic nucleus. In the compounds of general Formulas III to VII, one of the basic substituent groups as represented by

is attached to any one of the carbon atoms of one of the benzenoid rings of the tricyclic nuclei and the other such basic substituent is attached to any one of the carbon atoms of the other benzenoid ring of the tricyclic nuclei.

Illustrative examples of straight or branched lower alkyl groups which $R^1$ and $R^2$ may represent in general Formulas I to VII are methyl, ethyl, n-propyl, isopropyl, n-butyl and tert-butyl.

Illustrative examples of straight or branched alkylene chains which A may represent are methylene, ethylene, propylene, isobutylene, 2,2-dimethylbutylene, 2-methylpropylene, and pentylene.

Illustrative examples of compounds of general Formula I are 3,9-bis(2-dimethylaminoethoxy)fluoranthene, 3,9-bis-(4-diethylaminobutoxy)fluoranthene, 3,8-bis(5-diallylaminopentoxy)fluoranthene, 2,7-bis(3-diisopropylamino-propyl/fluorene, 2,7-bis(2-dibutylaminoethoxy)fluorene, 3,6-bis(3-dimethylaminoisobutoxy)fluoren-9-ol, 2,7-bis(2-dimethylaminoethoxy)fluoren-9-ol, 2,7-bis(3-diethylaminopropoxy)-fluoren-9-one, 2,5-bis(2-aminoethoxy)fluoren-9-one, 3,6-bis(4-dimethylaminobutoxy)carbazole, 2,7-bis(5-diethylamino-2,2-dimethylbutoxy)fluorene, N-ethyl 3,6-bis(4-diallylaminobutoxy)carbazole, 3,9-bis(3-diethylaminopropylthio)fluoranthene, 2,7-bis(4-methylaminobutylthio)-fluoren-9-one, 2,7-bis(3-dimethylaminoacetyl)fluorene, 3,9-bis(4-diethylaminobutyryl)fluoren-9-one, 2,6-bis(4-dipropylaminobutoxy)anthraquinone, 2,7-bis(3-dimethylaminopropoxy)anthraquinone, 2,5-bis(-diisobutylaminopropionyl)fluorene, 2,8-bis(5-diallylaminovaleryl)fluorene, 3,6-bis(4-diethylaminobutyryl)carbazole, and N-n-propyl 3,6-bis(3-diethylaminopropionyl)carbazole.

Pharmaceutically acceptable acid addition salts of the base compounds of this invention are those of any suitable inorganic or organic acid. Illustrative suitable inorganic acids are hydrochloric, hydrobromic, sulfuric, and phosphoric acids. Illustrative suitable organic acids are lower aliphatic hydrocarbon monocarboxylic acids, such as, glycolic or lactic acid; lower aliphatic lower alkoxyhydrocarbon monocarboxylic acids, such as, methoxyacetic or ethoxyacetic acids; lower aliphatic lower alkanoyl-hydrocarbon monocarboxylic acids, such as, pyruvic acid; lower aliphatic hydrocarbon dicarboxylic acids, such as malonic, succinic, methylsuccinic, glutaric, α-methylglutaric, β-methylglutaric, itaconic, maleic, citraconic, homocitraconic, or fumaric acid; lower aliphatic hydroxy hydrocarbon dicarboxylic acids, such as, malic or tartaric acid; lower aliphatic lower alkoxy-hydrocarbon dicarboxylic acids, such as, α,β-dimethoxysuccinic or ethoxymaleic acid; lower aliphatic hydrocarbon tricarboxylic acids, such as, aconitic or tricarballylic acid; lower aliphatic hydroxyhydrocarbon tricarboxylic acids, such as, citric acid. Additionally organic sulfonic acids, such as lower alkane sulfonic acids, for example, methanesulfonic or ethanesulfonic acid, or lower hydroxy-alkane sulfonic acids, for example, 2-hydroxyethane sulfonic acid are suitable. Particularly useful are pharmacologically acceptable acid addition salts with mineral acids, such as hydrochloric acid. Mono- or di-acid salts may be formed, and the salts may be hydrated, for example, monohydrate, or substantially anhydrous.

Introduction of an antigen, or a foreign substance, into an organism results in a specific immunological response changing the reactivity of the organism towards the antigen and substances closely resembling the antigen. This response is usually a heightened reactivity to the antigen. This heightened reactivity is due in part to the production of antibodies which can result in an immediate hypersensitivity and in part to a cell-mediated immunity which can result in delayed hypersensitivity. Cell-mediated immunity is dependent upon the presence of cells sensitized to antigen, primarily thymus-modified lymphocytes, which specifically interact with the antigen. Macrophages are also involved in the processing of antigen and in the effector mechanisms leading to dealyed hypersensitivity.

The type of substances which elicit delayed hypersensitivity are many and various. They may be organic chemicals, including drugs, simple chemical derivatives, or protein-containing antigens of micro-organisms, such as, bacteria, viruses, fungi or protozoa, or tissue antigens. Conditions of delayed hypersensitivity are associated with numerous pathological disorders, for example, contact hypersensitivity in the skin, rejection of tissue grafts or transplants, autoimmune diseases and certain infectious diseases. Such pathological disorders often involve, in addition to the cell-mediated delaysd hypersensitivity responses, humoral antibody responses involving the production of antigen-specific antibodies. Generally, treatment of these disorders has been with immunosuppressive agents, such as, purine analogs, folic acid antagonists, alkylating agents and corticosteroids. Such agents have been found to be non-specific in their immunosuppressant effects, that is they suppress both the humoral antibody and delayed (cell-mediated) hypersensitivity responses. [Drug Therapy 1, no. 4, pp. 3–16 (1971)]. The compounds disclosed herein are unique in that they suppress only the delayed hypersensitivity response without concurrent suppression of the humoral immune response.

The compounds disclosed herein suppress delayed hypersensitivity responses thereby rendering the compounds useful in patients in the treatment of conditions of delayed hypersensitivity resulting from infectious diseases, specifically tuberculosis, streptococcus, staphylococcus and pneumococcus diseases, typhoid fever, undulant fever, chancroid, whooping-cough and leprosy; toxoids and vaccines, particularly diphtheria toxoid and smallpox vaccination; contact hypersensitivity in the skin, specifically from nickel salts, primrose or poison ivy, poison oak and paraphenylene diamine; rejection of tissue grafts and transplants; and autoimmune diseases, specifically rheumatoid arthritis, systemic lupus erythematosus, glomerular nephritis, rheumatic fever, ulcerative colitis, diabetes mellitus, pernicious anemia, coeliac disease, primary atypical pneumonia, Hashiomoto's thyroiditis, multiple sclerosis, peripherial neuritis, pemphigus, Addison's disease and Grave's disease.

The utility of the compounds disclosed herein in the treatment of conditions of delayed hypersensitivity is manifested by the ability of the compounds to suppress delayed hypersensitivity reaction in vitro in the macrophage migration inhibition test (MMIT) and in vivo in the experimental allergic encephalomyelitis (EAE) test, which are well recognized tests for detecting agents or compounds effective in treating conditions of delayed hypersensitivity. *Immunology for Students of Medicine*, 3rd edition, 1970, F. A. Davis Company, pp. 498-500; Federation Proceedings 27, No. 1, pp. 3–15, (1968); Advances in Immunology 5, pp. 131–208 (1966).

As used herein, the term patient means warm blooded animals, particularly mammals and humams. The compounds disclosed herein may be administered to a patient orally, parenterally, or topically either alone or in the form of pharmaceutical preparations. Pharmaceutical preparations containing conventional pharmaceutical carriers and as active ingredients compounds of this invention can be employed in unit dosage forms such as solids, for example, tablets, capsules and pills, or liquid solutions, suspensions, or emulsions for oral and parenteral administration. The quantity of compound administered can vary over a wide range to provide from about 0.1 mg/kg (milligrams per kilogram) to about 200mg/kg of body weight of the patient per day, and preferably from about 1 mg/kg to 100mg/kg of body weight of the patient per day, to achieve the desired effect. Unit doses can contain from about 5 mg to 1.0 g of a compound of this invention and may be administered, for example, from 1 to 4 times daily.

The compounds of general Formula I wherein Y is oxygen or divalent sulfur, that is, bis-amino ether and thioether derivatives may be prepared by the reaction of one equivalent of a diol or dithiol derivative of the formula $$HR^4 + W + R^4H \qquad \text{Formula VIII}$$

wherein $R^4$ represents oxygen or divalent sulfur; and [W] represents fluoranthene, fluorene, fluoren-9-ol, fluoren-9-one, carbazole, N-(lower)alkyl carbazole, or anthraquinone; with two equivalents of a aminoalkylhalide of the formula $$Hal-A-N\begin{matrix} R^1 \\ R^2 \end{matrix} \qquad \text{Formula IX}$$

wherein Hal represents chlorine, bromine or iodine; A is a straight or branched alkylene chain of from 1 to 6 carbon atoms; and each of $R^1$ and $R^2$ is hydrogen, straight or branched lower alkyl of from 1 to 4 carbon atoms, or alkenyl of 3 to 6 carbon atoms having the vinyl unsaturation in other than the 1-position, in the presence of a base. Typical aminoalkyl halides are, for example, 2-diethylaminoethylchloride, 3-dimethylaminopropylbromide, 3-dipropylaminoisobutylchloride, and 3-diallylaminopropylchloride.

Alternatively the bis-aminoalkylene ether and thioether derivatives of general Formula I may be prepared by the reaction of a bis-ω-haloalkylether or thioether derivative of the formula $$Hal-A-R^4 + W + R^4-A-Hal \qquad \text{Formula X}$$

wherein Hal, A, $R^4$ and [W] have the meanings defined hereinabove with an amine of the formula $$HN\begin{matrix} R^1 \\ R^2 \end{matrix}$$

wherein $R^1$ and $R^2$ have the meanings defined hereinabove. The bis-ω-haloalkyl ether and thioether derivatives of Formula X are obtained by the reaction of a diol or dithiol derivative of [W] with a haloalkylhalo, that is, Hal-A-Hal wherein Hal and A have the meanings defined hereinabove, in the presence of a base.

Suitable bases for the above described reaction are sodium methoxide, sodium hydride, sodium amide, sodium hydroxide, and potassium hydroxide. Suitable solvents include aromatic hydrocarbons, such as benzene, toluene and xylene; halogenated aromatics, such as, chlorobenzene; aprotic solvents, such as, N,N-dimethylformamide, N,N-dimethylacetamide, and dimethylsulfoxide; alcohols, such as, ethanol or isopropyl alcohol; ketones, such as, acetone, ethers, such as, tetrahydrofuran or dioxane; water; or mixtures of these solvents.

When either soidum methoxide, sodium amide or sodium hydride, for example, is used as the base, the reaction is carried out in an anhydrous medium, such as anhydrous toluene or chlorobenzene. About 2.5 equivalents of the base is added to a suspension of a diol or dithiol derivative of Formula VIII, in the anhydrous solvent, and the mixture is heated. In the case where sodium methoxide is used, the methanol formed may be removed advantageously by azeotropic distillation. About 2.5 equivalents of the halide, either an aminoalkylhalide or a haloalkylhalo derivative is added, and the mixture heated to reflux for a period which may vary from about 4 to 24 hours. The products are isolated by customary procedures.

In the method where an alkali hydroxide, such as potassium hydroxide is used as the base, two different procedures may be used. In the one procedure a 25 to 50 per cent aqueous solution of the alkali hydroxide (about 2.5 equivalents) is added to a suspension of a diol or dithiol derivative of Formula VIII in a suitable aromatic solvent, for example xylene. This mixture is then heated to boiling, stirring being optional, and the water removed by azeotropic distillation. The reaction mixture, now being essentially anhydrous, is treated with about 2.5 equivalents of either an aminoalkylhalide or a haloalkylhalo derivative. In the other procedure the reaction is carried out in a heterogenous medium of water and an aromatic hydrocarbon, such as, toluene or xylene. For example, one equivalent of a diol or dithiol derivative of Formula VIII is suspended in the aromatic hydrocarbon. To this suspension is added about 2.5 equivalents of a hydrohalide salt of an aminoalkylhalide derivative or a haloalkylhalo derivative in a minimum volume of water after which a 25 to 50% solution of the alkali hydroxide (about 5 equivalents when using an aminoalkylhalide derivative and about 2 equivalents when using a haloalkylhalo derivative) is added with efficient stirring. This mixture is heated to reflux for about 6 to 24 hours, and the product is isolated from the hydrocarbon layer. The reaction between the bis-ω-haloalkylether or thioether derivative of Formula X and an appropriate amine may be carried out under a variety of conditions. For example, the compound of Formula X may be heated together with a large excess of the amine, the excess amine serving as both the reaction medium and the hydrohalide acceptor. Or, 1 equivalent of the bis(ω-haloalkyl)ether or thioether, and 4 equivalents of the amine may be heated together in one of a number of different types of solvents, for example, in aromatic solvents, such as, benzene, toluene, xylene, or chlorobenzene; or lower molecular weight alcohols, such as, methanol, ethanol or isopropyl alcohol; or lower molecular weight ketones, such as, acetone or methyl ethyl ketone. The reaction between the halo compound and the amine is usually promoted by the addition of either sodium or potassium iodide, the iodide being used in either catalytic or stoichiometric amounts. In some cases, it may be advantageous to use only 2 equivalents of the amine for each equivalent of the bis-ω-haloalkylether or thioether, an excess of either powdered potassium carbonate or sodium carbonate being used as the hydrohalide acceptor.

Additional methods for the preparation of bis-aminoalkylene ether and thioether derivatives of fluoranthene are set forth in U.S. Pat. No. 3,707,471; of fluorene, fluoren-9-ol, and fluoren-9-one are set forth in U.S. Pat. Nos. 3,592,819 and 3,692,907; and of 2,6- and 2,7-bis-piperidinoalkylene ether anthraquinone derivatives are set forth in Belgian patent 767-201; and the appropriate portions or each disclosure are incorporated herein by reference thereto. The additional methods set forth in these disclosures may be appropriately applied to the preparation of bis-aminoalkylene ether and thioether derivatives of, carbazole, N-(lower)alkyl carbazole, and anthraquinone wherein the position of substitution is other than 2,6- or 2,7-.

The compounds of general Formula I wherein Y is carbonyl, and [W] represents fluoranthene, fluorene, carbazole, and N(lower)alkyl carbazole, may be prepared by an amination reaction of a bis-ω-haloalkanoyl derivative of the formula

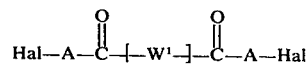   Formula XI wherein Hal is chlorine, bromine or iodine; A is a straight or branched alkylene chain of from 1 to 6 carbon atoms; and [W¹] represents fluoranthene, fluorene, carbazole, or N-(lower)alkyl carbazole; with an amine of the formula

wherein $R^1$ and $R^2$ have the meanings defined in general Formula I.

The amination reaction may be carried out under a variety of conditions. For example, a compound of Formula XI may be heated together with a large excess of the amine, the excess amine serving as the reaction medium and the hydrohalide acceptor. Or, one equivalent of a compound of Formula XI and four equivalents of the amine, may be heated together in one of a number of different types of solvents, for example, in aromatic solvents, such as, benzene, toluene, or xylene; ethers, such as, tetrahydrofuran, or dioxane; ketones, such as, acetone or butanone; aprotic solvents, such as N,N-dimethylformamide, N,N-dimethylacetamide, or dimethyl sulfoxide; or mixtures of these solvents with water. The reaction between a compound of Formula XI wherein Hal is Cl and the amine is frequently promoted by the addition of either sodium iodide or potassium iodide, the iodide being used in either catalytic or stoichiometric amounts. In some cases, it may be advantageous to use only two equivalents of the amine for each equivalent of the bis-ω-haloalkanoyl derivative, an excess of an inorganic base, such as, powdered sodium carbonate or potassium carbonate being used as the hydrohalide acceptor. The reaction will proceed normally in 12 hours to two weeks at temperatures of from −30° to 150°C.

Alternatively, the amination reaction may be carried out on a derivative of a compound of Formula XI, such as, the bis-ketal derivative that may be prepared by allowing the bis-ω-haloalkanoyl derivative and an excess of ethyl orthoformate to react in the presence of an acid catalyst such as hydrochloric acid for several days in a polar solvent such as ethanol or tetrahydrofuran.

The bis-ω-haloalkanoyl derivatives of Formula XI can be prepared by a Friedel-Crafts acylation reaction of an appropriate aromatic polycyclic compound as represented by [W¹]. Suitable acylating agents which may be used are, for example, chloroacetyl chloride, bromoacetyl bromide, 3-chloropropionyl chloride, 4-chlorobutyryl chloride, 5-chloro-4-methylvaleryl chloride and 4-chloro-3-ethylbutyryl chloride.

The acylation reaction may be carried out in a variety of solvents and under catalysis of a variety of Lewis acids. The temperature and duration of the reaction may be varied to allow for optimum reaction conditions. A preferred procedure is to combine one equivalent of an appropriate aromatic polycyclic compound as represented by [W¹] with 2.5 equivalents of an acylating agent in methylene chloride followed by portionwise addition of aluminum chloride. The temperature of the reaction is maintained below zero degrees with continuous stirring. After the additions are complete the temperature may be elevated to 25°–40°C for 12 to 36 hours. The reaction mixture is worked up in the usual manner by decomposing the complex with ice water/HCl. The product obtained is recrystallized from methylene chloride, chloroform, or the like. The procedure may be varied such that there is a reverse addition of acylating agent and Lewis acid, or a reverse addition of aromatic polycyclic compound and Lewis acid. The more reactive halogen derivative, that is, the bis-ω-iodoalkanoyl derivative, may be prepared from the corresponding bis-chloro derivative using a halogen exchange reaction under the conditions generally employed in the Conant-Finkelstein reaction.

The acylation reaction described above results in bis-ω-haloalkanoyl derivatives of Formula XI wherein the position of substitution on the various aromatic polycyclic compounds is the following: 3,9-bis-ω-haloalkanoylfluoranthene; 2,7-bis-ω-haloalkanoylfluorene; 3,6-bis-ω-haloalkanoylcarbazole; or N-(lower)alkyl carbazole.

The bis-aminoalkanoyl derivatives of general Formula I wherein [W] represents fluoranthene, fluorene, carbazole, or N-(lower)alkylcarbazole, A is an alkylene chain of from 3 to 6 carbon atoms and $R^1$ and $R^2$ are other than hydrogen may be prepared by the reaction of a dinitrile derivative of the formula

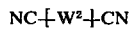   Formula XII wherein [W²] represents fluoranthene, fluorene, carbazole, or N-(lower)alkylcarbazole with a Grignard reagent of the formula

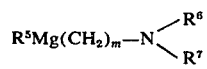   Formula XIII wherein $R^5$ is bromine or chlorine; m is an integer of from 3 to 6; and $R^6$ and $R^7$ are straight or branched lower alkyl of from 1 to 4 carbon atoms or alkenyl of 3 to 6 carbon atoms having the vinyl unsaturation in other than the 1-position. The reaction will proceed in from 1 to 24 hours at a temperature ranging from room temperature to about 80°C. The Grignard reagent may be prepared by reacting magnesium and an aminoalkyl $C_{3-6}$ halide wherein the halide is bromine or chlorine; a preferred solvent for this reaction is tetrahydrofuran. The dinitrile derivatives of Formula XII may be prepared from known diamines by a Sandmeyer reaction on the tetrazonium salts or from known dicarboxylic acid derivatives by dehydration of the corresponding amides by standard procedures.

The bis-aminopropionyl derivatives of general Formula I wherein [W] represents fluoranthene or fluorene, and both of $R^1$ and $R^2$ are not hydrogen, may also be prepared by a Mannich reaction of a bis-acetyl derivative of the formula

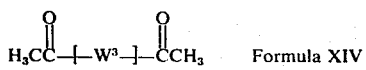 Formula XIV wherein [W³] represents fluoranthene or fluorene, with an amine of the formula

wherein R¹ and R² have the meanings defined in general Formula I with the proviso that both R¹ and R² are not hydrogen, in the presence of formaldehyde. By combining one equivalent of a compound of Formula XIV and two or more equivalents an amine with three or more equivalents of formaldehyde the reaction will proceed in from a few minutes to 24 hours in solvents such as water, acetic acid, ethanol, butanol, dioxane, and tetrahydrofuran and at temperatures equivalent to the reflux temperature of the solvent. In this reaction either of two sources of formaldehyde may be employed. When formalin is used the reaction may be conducted with a suspension of a compound of Formula XIV or a co-solvent such as methanol may be added to allow the reaction to proceed in a homogeneous medium. When the source of formaldehyde is paraformaldehyde the reaction is carried out in an organic solvent such as those mentioned above. It is sometimes desirable to add a slight excess of hydrochloric acid to promote depolymerization of paraformaldehydr either during the reaction or at the end of the reaction.

The amine employed in this reaction may be added to the reaction medium as the hydrochloride salt or as the base form with subsequent in situ formation of the hydrochloride salt by the addition of hydrochloric acid.

The bis-acetyl derivatives of Formula XIV may be prepared by a Friedel-Crafts acylation reaction on fluoranthene or fluorene, or by a reaction of a bis-acid chloride derivative of fluoranthene or fluorene with dimethylcadmium which can be prepared from methyl Grignard and cadmium chloride. The bis-acid chlorides can be prepared by conventional procedures.

The bis-aminoalkanoyl derivatives of fluoren-9-one, that is, compounds of general Formula I wherein Y is carbonyl and [W] represents fluoren-9-one can be prepared by oxidation of the corresponding fluorene bis-aminoalkanoyl derivatives, the preparations of which are described hereinabove. This oxidation reaction may be carried out using dichromate anion such as sodium dichromate or potassium dichromate as the oxidizing agent. The reaction will proceed in from 15 minutes to 6 hours at a temperature of from 80°C to 120°C. The amount of oxidizing agent is limited to the stoichiometric quantity required for oxidation of the 9-methylene group of the fluorene derivative. Suitable solvents for this conversion are, for example, water, acetic acid and tert-butyl alcohol, or combinations of these solvents. For example, by combining three moles of a bis-aminoalkanoyl fluorene derivative of general Formula I, wherein Y is carbonyl, and [W] is fluorene, dissolved in acetic acid with four moles of sodium dichromate and refluxing the mixture for 1 to 3 hours, the corresponding fluoren-9-one derivative is obtained.

Additional methods for the preparation of compounds of general Formula I wherein Y is carbonyl and [W] is fluoren-9-one are set forth in Great Britain patent 1,286,755.

The following specific examples are illustrative of the compounds of general Formula I.

EXAMPLE 1

Bis(3-diethylaminopropoxy)fluoranthene dihydrochloride

To 200 ml of water containing 16.0 g (0.4 mole) of sodium hydroxide and 15.7 g (0.067 mole) of 3,9-dihydroxyfluoranthene are added 200 ml of toluene and 27.9 g (0.15 mole) of 3-diethylaminopropyl chloride hydrochloride, and the heterogeneous reaction mixture is stirred at reflux for 24 hours. After cooling, the organic layer is washed with water, dried over magnesium sulfate, and concentrated in vacuo. The residue is crystallized from ether to give 3,9-bis(3-diethylaminopropoxy)-fluoranthene which is converted to the dihydrochloride salt with ethereal HCl and recrystallized from methanolbutanone, M.P. 235°–236.5°C.

EXAMPLE 2

3,9-Bis(2-diethylaminoethoxy)fluoranthene dihydrochloride

When 2-(diethylamino)ethyl chloride hydrochloride is used in place of 3-(diethylamino)propyl chloride hydrochloride, and the procedure of Example 1 is followed, 3,9-bis(2-diethylaminoethoxy)fluoranthene dihydrochloride is obtained. M.P. 220°–222°C.

EXAMPLE 3

3,9-Bis(3-diethylaminopropylthio)fluoranthene dihydrochloride

When in the procedure of Example 1, fluoranthene-3,9-dithiol is substituted for 3,9-dihydroxyfluoranthene, 3,9-bis(3-diethylaminopropylthio)fluoranthene dihydrochloride is obtained.

EXAMPLE 4

3,9-Bis(2-dimethylamino-1-methylethoxy)fluoranthene

To 450 ml of chlorobenzene is added 10.6 g (0.033 mole) of fluoranthene-3,9-diol diacetate, 10.4 g (0.066 mole) of 2-dimethylamino-1-methylethyl chloride hydrochloride and 7.2 g (0.132 mole) of sodium methoxide, and the mixture is stirred at reflux for 24 hours, then cooled and filtered. The filtrate is washed with several portions of water and dried over anhydrous magnesium sulfate. The chlorobenzene is evaporated in vacuo, leaving an oily residue which is chromatographed as the free base on alumina using chloroform as the eluant to give 3,9-bis-(2-dimethylamino-1-methylethoxy)fluoranthene. $\lambda_{max}^{EtOH}$ 243, $E_1 \ cm^{1\%}$ 1060.

The preparation of additional Examples of bis-amine ether and thioether derivatives of anthraquinone are set forth in U.S. Pat. No. 3,707,471 and the appropriate Examples disclosed therein are incorporated herein by reference thereto.

EXAMPLE 5

2,7-Bis(2-diethylaminoethoxy)fluoren-9-one dihydrochloride

A solution of 2-diethylaminoethyl chloride [obtained from 15.5 g (0.09 mole) of 2-diethylaminoethyl chloride hydrochloride] in 100 ml of toluene (dried over molecular sieves) is added to a mixture of 6.4 g (0.03 mole) of 2,7-dihydroxyfluoren-9-one and 3.3 g (0.06 mole) of sodium methoxide in 200 ml of toluene (dried over molecular sieves). This mixture is heated to reflux with stirring for three hours. Upon cooling, the mixture is filtered to remove the precipitated sodium chloride. The toluene solution is washed three times with water, then once with a saturated sodium chloride solution and dried over anhydrous magnesium sulfate. This mixture is filtered, and the filtrate acidified to Congo Red with ethereal hydrogen chloride. The solid which precipitates is filtered, recrystallized from butanone with enough methanol added to effect solution, and the product dried at 100°C for 24 hours under vacuum to give 2,7-bis(2-diethylaminoethoxy)fluoren-9-one dihydrochloride. M.P. 235°–237°C.

EXAMPLE 6

2,7-Bis(2-butylmethylaminoethoxy)fluoren-9-one dihydrochloride

When in the procedure of Example 5, 2-butylmethylaminoethyl chloride is substituted for 2-diethylaminoethyl chloride, 2,7-bis(2-butylmethylaminoethoxy)fluorne-9-one dihydrochloride is obtained. M.P. 240°–243°C.

EXAMPLE 7

2,7-Bis(2-dimethylaminoethoxy)fluoren-9-one dihydrochloride

A. To a stirred, refluxing mixture of 21.2 g (0.10 mole) of 2,7-dihydroxyfluoren-9-one and 43.0 g (0.30 mole) of 1-bromo-2-chloroethane in 400 ml of water is added dropwise, over a period of 30 minutes, 80 ml (0.20 mole) of 10% aqueous sodium hydroxide. After complete addition of the alkali, the mixture is refluxed with stirring for eighteen hours. Upon cooling, the supernatant water layer is decanted and the residue taken up in ethanol. The solid that separates is filtered, washed with ethanol, and dried in the air, M.P. 161°–174°C. The material is dissolved in chloroform, washed with 10% aqueous sodium hydroxide, with water and dried over anhydrous magnesium sulfate. The mixture is filtered, the solvent evaporated, the residue recrystallized from a mixture of five parts ethanol to one part chloroform and the product air dried to give intermediated 2,7-bis(2-chloroethoxy)fluoren-9-one, M.P. 135°–139°C.

B. A mixture of 4.4 g (0.013 mole) of 2,7-bis(2-chloroethoxy)fluoren-9-one, 2 g (of potassium iodide and 100 ml of 40% aqueous dimethylamine in 50 ml of tetrahydrofuran is heated with stirring at 122°C for sixteen hours in a Parr pressure reactor. The solvent is removed in vacuo and the residue taken up in water. The aqueous solution is made basic with 10% sodium hydroxide and extracted with ether. The ether solution is washed twice with water, then with saturated sodium chloride solution and dried over anhydrous magnesium sulfate. The mixture is filtered and the filtrate acidified to Congo Red with ethereal hydrogen chloride. The ether is decanted from the oil which precipitates and the oil recrystallized, once from butanone with enough methanol added to effect solution, and twice from methanol alone. The product obtained is dried at 100°C under vacuum to give 2,7-bis(2-dimethylaminoethoxy)-fluoren-9-one dihydrochloride. M.P. 278°–280°C (dec.).

EXAMPLE 8

2,7-Bis(2-diethylaminoethoxy)fluorene dihydrochloride

A solution of 2-diethylaminoethyl chloride [obtained from 12.9 g (0.075 mole) of 2-diethylaminoethyl chloride hydrochloride] in 100 ml of toluene (dried over molecular sieves) is added to a mixture of 4.9 g (0.025 mole) of 2,7-dihydroxyfluorene and 2.7 g (0.05 mole) of sodium methoxide in 200 ml of toluene (dried over molecular sieves). This mixture is refluxed with stirring for three hours. Upon cooling the mixture is filtered to remove the precipitated sodium chloride. The toluene solution is washed three times with water, then once with a saturated sodium chloride solution and dried over anhydrous magnesium sulfate. This mixture is filtered and the filtrate acidified to Congo Red with ethereal hydrogen chloride. The solid which precipitates is filtered, dissolved in butanone with enough methanol added to effect solution, decolorized with charcoal, and the product obtained at 80°C under vacuum, 2,7-bis(2-diethylaminoethoxy)fluorene dihydrochloride. M.P. 213°–216°C.

EXAMPLE 9

2,7-Bis(2-diethylaminoethoxy)fluoren-9-ol dihydrochloride

A total of 2.3 g (0.06 mole) of sodium borohydride is added in small portions to a stirred solution of 9.7 g (0.02 mole) of 2,7-bis(2-diethylaminoethoxy)fluoren-9-one dihydrochloride in 200 ml or methanol, maintaining the mixture at 0°C throughout the addition. The mixture is allowed to warm to room temperature and the solvent removed in vacuo. The residue is taken up in 10% hydrochloric acid, the mixture extracted with ether, and the aqueous acidic solution evaporated in vacuo. The residue is dissolved in methanol, cooled at −20°C, and the inorganic material which precipitates removed by filtration. The filtrate is evaporated in vacuo, the residue dissolved in water and made basic with 10% aqueous sodium hydroxide. The liberated free base is extracted into ether, the ether extract washed with water and dried over anhydrous magnesium sulfate. The mixture is filtered, the filtrate evaporated, the residue taken up in isopropyl alcohol and acidified to Congo Red with ethereal hydrogen chloride. The precipitated product is collected and recrystallized three times from a mixture of isopropyl alcohol and methanol to give 2,7-bis(2-diethylaminoethoxy)-fluoren-9-ol dihydrochloride. M.P. 192°–194°C.

EXAMPLE 10

2,7-Bis(3-dibutylaminopropoxy)fluorene dihydrochloride

When in the procedure of Example 8, 3-dibutylaminopropyl chloride is substituted for 2-diethylaminoethyl chloride, 2,7-bis(3-dibutylaminopropoxy)fluorene is obtained. M.P. 170°–172°C.

EXAMPLE 11

2,7-Bis(2-diethylaminoethylthio)fluorene dihydrochloride

When in the procedure of Example 8, fluorene-2,7-dithiol is substituted for 2,7-dihydroxyfluorene, 2,7-bis-(2-diethylaminoethylthio)fluorene dihydrochloride is obtained.

The preparation of additional Examples of bis-amine ether and thioether derivatives of fluorene, fluoren-9-ol and fluoren-9-one are set forth in U.S. Pat. Nos. 3,592,819 and 3,692,907, and the appropriate Examples disclosed therein are incorporated herein by reference thereto.

EXAMPLE 12

N-Ethyl-3,6-carbazolediol

To 700 ml of water containing 80 g (2.0 mole) of sodium hydroxide is added 85 g (0.27 mole) of N-ethyl-3,6-carbazolediol diacetate. The reaction mixture is heated for one hour then acidified with 3N hydrochloric acid to give N-ethyl-3,6-carbazolediol which is recrystallized from ethanol-water. M.P. 190°–200°C (dec.).

EXAMPLE 13

3,6-Bis(2-diethylaminoethoxy)-N-ethylcarbazole bis-dihydrogen citrate hemihydrate To 350 ml of water containing 25 g (0.62 mole) of sodium hydroxide is added 22.7 g (0.1 mole) of N-ethyl-3,6-carbazolediol, 68.7 g (0.4 mole) of 2-diethylaminoethylchloride hydrochloride and 700 ml of toluene. The heterogeneous reaction mixture is refluxed with stirring for 24 hours, after which the toluene layer is separated, washed with several portions of water, dried and evaporated in vacuo. The resulting oily residue is purified by column chromatography on alumina using ether as the eluant. The product is converted to the bis-dihydrogen citrate salt and recrystallized from methanol-butanone. M.P. 100°–105°C.

EXAMPLE 14

3,6-Bis(2-diethylaminoethoxy)-N-ethylcarbazole dihydrochloride

A mixture of 15.5 g (0.05 mole) of N-ethyl-3,6-carbazolediol diacetate, 17.2 g (0.1 mole) of 2-diethylaminoethylchloride hydrochloride, 10.8 g (0.2 mole) of sodium methoxide and 400 ml of chlorobenzene is refluxed for 24 hours. Upon cooling, the reaction mixture is filtered, and the filtrate is washed with several portions of water, dried over anhydrous magnesium sulfate, diluted with ether and acidified with ethereal HCl. The resulting precipitate is separated and recrystallized from methanol-ethyl acetate to give 3,6-bis(2-diethylaminoethoxy)-N-ethylcarbazole dihydrochloride. M.P. 208°–210°C.

EXAMPLE 15

3,6-Bis(3-dimethylaminopropoxy)-N-ethylcarbazole dihydrochloride

Following the procedure of Example 14, only substituting for 2-diethylaminoethylchloride hydrochloride, 15.8 g (0.1 mole) of 3-dimethylaminopropylchloride hydrochloride, 3,6-bis(3-dimethylaminopropoxy)-N-ethylcarbazole dihydrochloride is obtained. M.P. 239°–240°C.

EXAMPLE 16

1,8-Bis(2-diethylaminoethoxy)carbazole bis-dihydrogen citrate

Following the procedure of Example 13, only substituting for N-ethyl-3,6-carbazolediol, 19.9 g (0.1 mole) of 1,8-carbazolediol and using 37.8 g (0.22 mole) of 2-diethylaminoethyl chloride hydrochloride, 1,8-bis(2-diethylaminoethoxy)carbazole bis-dihydrogen citrate is obtained.

EXAMPLE 17

3,6-Bis(2-diethylaminoethoxy)-N-methylcarbazole bis-dihydrogen citrate

Following the procedure of Example 13, only substituting for N-ethyl-3,6-carbazolediol, 21.3 g (0.1 mole) of N-methyl-3,6-carbazolediol, 3,6-bis(2-diethylaminoethoxy)-N-methylcarbazole bis-dihydrogen citrate is obtained.

EXAMPLE 18

3,6-Bis(2-dihexylaminoethoxy)-N-ethylcarbazole dihydrochloride

Following the procedure of Example 14, only substituting for 2-diethylaminoethylchloride hydrochloride, 28.4 g (0.1 mole) of 2-dihexylaminoethylchloride hydrochloride, 3,6-bis(2-dihexylaminoethoxy)-N-ethylcarbazole dihydrochloride is obtained.

EXAMPLE 19

3,6-Bis(2-ethylaminoethoxy)-N-ethylcarbazole dihydrochloride

A. To a stirred mixture of 31.3 g (0.1 mole) of N-ethyl-3,6-carbazolediol diacetate and 39.4 g (0.3 mole) of 1-bromo-2-chloroethane in 400 ml chlorobenzene is added 0.2 mole of sodium methoxide. Upon complete addition of the alkali, the mixture is refluxed with stirring for 18 hours, then cooled. The supernatant water layer is decanted and the residue is taken up in ethanol-chloroform to give 3,6-bis(2-chloroethoxy)-N-ethylcarbazole.

B. A mixture of 35.2 g (0.1 mole) of 3,6-bis(2-chloroethoxy)-N-ethylcarbazole, 4.5 g (0.1 mole) of ethylamine, 2.0 g of potassium iodide and 100 ml of tetrahydrofuran is heated with stirring at 100°C for 24 hours in a Parr pressure reactor. The solvent is removed in vacuo, and the remaining residue is treated with dilute sodium hydroxide and ether. The ether layer is washed twice with water, dried over magnesium sulfate and acidified with ethereal HCl to give 3,6-bis(2-ethylaminoethoxy)-N-ethylcarbazole dihydrochloride which is recrystallized from methanol-ethyl acetate.

EXAMPLE 20

3,6-Bis(2-diethylaminoethylthio)-N-ethylcarbazole dihydrochloride

When in the procedure of Example 14, N-ethyl-carbazole-3,6-dithiol is substituted for N-ethyl-3,6-carbazolediol, 3,6-bis(2-diethylaminoethylthio)-N-ethylcarbazole dihydrochloride is obtained.

EXAMPLE 21

2,6-Bis(2-diethylaminoethoxy)anthraquinone dihydrochloride

A. A solution of 12 g (0.3 mole) of sodium hydroxide in 15 ml of water is added, with efficient stirring, to a boiling mixture of 36 g (0.15 mole) of 2,6-dihydroxyanthraquinone suspended in 250 ml of xylene. With continued stirring, the mixture is heated to reflux, the water being removed from the mixture by collection in a Dean-Stark distilling receiver. When all of the water has been removed, a solution of 2-diethylaminoethyl chloride in 250 ml of xylene is added. This solution is prepared by dissolving 100 g (0.58 mole) of 2-diethylaminoethyl chloride hydrochloride in 20 ml of water, covering the solution with 200 ml of xylene, chilling the mixture to about −5°C, and with rapid stirring, adding a solution of 45 g of potassium hydroxide in 35 ml of water. The xylene layer is decanted from the thick slurry of inorganic salt and water, which is washed with another 50 ml of xylene. The combined xylene extracts are dried with anhydrous magnesium sulfate and filtered. With continued rapid stirring, the resulting mixture is heated to reflux for another 28 hours.

B. The mixture is poured into 500 ml of water. The yellow solid which separates at the xylene/water interface is removed by filtration with suction, washed thoroughly with hot water and dried. This major portion of the free base, M.P. 177°–180°C, is recrystallized from a mixture of hot methanol and a small volume of chloroform to give the pure base, M.P. 179°–180°C. Another 5–10 per cent of base can be obtained by working up the xylene layer. The pure base is dissolved in chloroform, the solution acidified to Congo Red with ethereal hydrogen chloride, diluted with ether, and the yellow precipitate filtered with suction. The dihydrochloride salt obtained is suspended in boiling methanol (15–20 ml per gram) and a vary small volume of water is added to effect solution. This solution is filtered, reduced about one-fourth in volume, diluted with additional methanol, then chilled. The recrystallized dihydrochloride is filtered and dried in a vacuum oven at 100°C to give 2,6-bis(2-diethylaminoethoxy)anthraquinone dihydrochloride, which melted with decomposition at 274°–275°C (or lower if the rate of heating the capillary tube was slower).

EXAMPLE 22

2,6-Bis(2-diisopropylaminoethoxy)anthraquinone dihydrochloride

With efficient stirring, 100 g (0.42 mole) of 2,6-dihydroxyanthraquinone is dissolved in 500–700 ml of about 10% potassium hydroxide solution. This solution is filtered to remove a small amount of insoluble material, then evaporated to dryness in a rotary evaporator. The reddish brown solid is dried in a vacuum oven at 100°C, ground to a fine powder, then redried at 100°C. A stirred suspension of 30 g of the powdered diphenoxide, containing about 24 g (0.075 mole) of the dipotassium salt of 2,6-dihydroxyanthraquinone, in 200 ml of xylene is heated to reflux and a small amount of water collected in the Dean-Stark distilling receiver. A solution of 2-diisopropylaminoethyl chloride in 100 ml of xylene, is added and the resulting mixture heated to reflux for about 24 hours. The reaction mixture is poured into water and worked up as in Example 21 (B) to give 2,6-bis(2-diisopropylaminoethoxy)anthraquinone dihydrochloride. M.P. 254°–256°C (dec.).

EXAMPLE 23

2,6-Bis(2-dimethylaminoethoxy)anthraquinone dihydrochloride

A well-stirred mixture of 12 g (0.05 mole) of 2,6-dihydroxyanthraquinone, 400 ml of chlorobenzene, 50 ml of methanol, and 5.4 g (0.10 mole) of sodium methoxide is heated to boiling, and the methanol distilled from the mixture. When the boiling point of the distillate reaches about 130°C, the mixture is allowed to cool below 100°C. Then, a solution of 2-dimethylaminoethyl chloride in 200 ml of chlorobenzene, prepared from 43.2 g (0.30 mole) of 2-dimethylaminoethyl chloride hydrochloride, is added and the resulting mixture heated to reflux with continued stirring for 24 hours. When cool, the mixture is poured into 400 ml of about one per cent sodium hydroxide solution. The aqueous layer is extracted with chloroform. The combined organic fractions are washed well with water, dried over anhydrous magnesium sulfate, filtered, and the solvents removed under reduced pressure in a rotary evaporator. The residue is dissolved in isopropyl alcohol and the solution acidified to Congo Red by the addition of ethereal hydrogen chloride. The dihydrochloride salt is recrystallized again from isopropyl alcohol to give 2,6-bis(2-diisopropylaminoethoxy)anthraquinone dihydrochloride. M.P. 278°–280°C (dec.).

EXAMPLE 24

2,7-Bis(2-diethylaminoethoxy)anthraquinone dihydrochloride

When in the procedure of Example 22, 2,7-dihydroxyanthraquinone and 2-diethylaminoethyl chloride are respectively substituted for 2,6-dihydroxyanthraquinone and 2-diisopropylaminoethyl chloride, 2,7-bis(2-diethylaminoethoxy)anthraquinone dihydrochloride is obtained. M.P. 232°–234°C (dec.).

The preparation of additional Examples of bis-amine ethers of anthraquinone are set forth in Belgian patent 767,210 and the appropriate Examples disclosed therein are incorporated herein by reference thereto.

EXAMPLE 25

3,9-Bis(dimethylaminoacetyl)fluoranthene dihydrochloride dihydrate

A mixture of 15.0 g (0.042 mole) of 3,9-bis(chloroacetyl)fluoranthene, 100 ml of 40% dimethylamine and 7.0 g of potassium iodide in 200 ml of butanone is placed in a Parr bomb and heated at 70°–80°C with stirring for 2 hours. The reaction mixture is cooled and poured into 2.0 liters of ice water, and the solid which precipitates is filtered off, dissolved in chloroform and dried over magnesium sulfate to give the free base of the desired product. The free base is converted to the dihydrochloride salt and recrystallized from methanol-acetone to give 3,9-bis(dimethylaminoacetyl)fluoranthene dihydrochloride dihydrate. M.P. 285°–288°C.

EXAMPLE 26

3,9-Bis(diethylaminoacetyl)fluoranthene dihydrochloride

Following the procedure of Example 25 only substituting for dimethylamine, 50 ml of diethylamine, 3,9-bis(diethylaminoacetyl)fluoranthene dihydrochloride is obtained. M.P. 248°–250°C.

EXAMPLE 27

3,9-Bis(4-diethylaminobutyryl)fluoranthene dihydrochloride

A solution of 15.0 g (0.037 mole) of 3,9-bis(4-chlorobutyryl)fluoranthene, 100 ml of diethylamine, 2.0 g of potassium iodide and 100 ml of tetrahydrofuran (THF) is heated at reflux with stirring for 3 days and filtered. The filtrate is poured onto ice water and the oil which separates is decanted and dissolved in ether. The ether solution is washed with a water-saturated sodium chloride solution, dried over magnesium sulfate and filtered. The filtrate is acidified with ethereal HCl, and the resulting precipitate is recrystallized twice from methanol-butanone to yield 3,9-bis(4-diethylaminobutyryl)fluoranthene dihydrochloride. M.P. 236°–239°C.

The preparation of additional Examples of bis-amine ketone derivatives of fluoranthene are set forth in Great Britain patent 1,304,561, and the appropriate Examples disclosed therein are incorporated herein by reference thereto.

EXAMPLE 28

2,7-Bis(diethylaminoacetyl)fluorene dihydrochloride

A mixture of 250 ml of tetrahydrofuran, 14.0 g (0.044 mole) of 2,7-bis(chloroacetyl)fluorene and 100 ml of diethylamine, previously cooled to 0°C, is stirred at room temperature for 54 hours, filtered and the filtrate evaporated to dryness. The residue is dissolved in ethanol, and this solution is treated with excess ethanolic hydrogen chloride to yield the dihydrochloride salt. The product is precipitated by the addition of a large volume of ether and purified by recrystallization from methanolethyl acetate. M.P. 225°–228°C.

EXAMPLE 29

2,7-Bis(5-diethylaminovaleryl)fluorene

A mixture of 30.0 g (0.074 mole) of 2,7-bis(5-chlorovaleryl)fluorene, 2.0 g of potassium iodide, 200 ml of diethylamine and 100 ml of tetrahydrofuran is stirred and heated in a Parr bomb at 120°C for 24 hours. The reaction mixture is combined with 300 ml of water, and the volume concentrated to 100 ml. Following the addition of 300 ml of water, the resulting precipitate is filtered and recrystallized once from ether-acetone and once from ether to yield 2,7-bis(5-diethylaminovaleryl)fluorene. M.P. 78°–80°C.

EXAMPLE 30

2,7-Bis(5-diethylaminovaleryl)fluoren-9-one

A solution of 12.0 g (0.025 mole) 2,7-bis(5-diethylaminovaleryl)fluorene, prepared in Example 29, 2.0 ml 40% benzyltrimethylammonium hydroxide in pyridine and 200 ml pyridine is stirred at room temperature while oxygen is bubbled through the solution at a rate of 500 ml/min. for a total of four hours. The reaction mixture is evaporated to dryness leaving a residue which is chromatographed on alumina using chloroform as the eluant. The solvent is removed from the reaction collected leaving a solid which is recrystallized once from chloroform-petroleum ether to yield 2,7-bis(5-diethylaminovaleryl)fluoren-9-one. M.P. 108°–109.5°C.

EXAMPLE 31

2,7-Bis(dimethylaminoacetyl)fluoren-9-one

A mixture of 15.0 g (0.045 mole) of 2,7-bis(chloroacetyl)fluoren-9-one, 100 ml of 40% dimethylamine and 7.0 g of potassium iodide in 200 ml of butanone is placed in a Parr bomb and heated at 70°–80°C with stirring for 2 hours. The reaction mixture is cooled and poured into 2 liters of ice water, and the solid which precipitates is filtered off, dissolved in chloroform and dried over magnesium sulfate to give 2,7-bis(-dimethylaminoacetyl)fluoren-9-one.

Additional Examples for the preparation of bis-amine ketone derivatives of fluorene and fluoren-9-one are set forth in Great Britain patent 1,286,755, and the appropriate Examples disclosed therein are incorporated herein by reference thereto.

EXAMPLE 32

3,6-Bis(4-dimethylaminobutyryl)-N-ethylcarbazole bis acid fumarate

A mixture of 15.8 g (0.039 mole) of 3,6-bis(4-chlorobutyryl)-N-ethylcarbazole, prepared from N-ethylcarbazole and 4-chlorobutyryl chloride, 75 ml of 40% aqueous dimethylamine and 2 g of potassium iodide in 175 ml of p-dioxane is heated in a reaction bomb with stirring for 44 hours. The reaction mixture is concentrated to one-half its original volume in vacuo and diluted with 500 ml of water. The semi-solid which separates is dissolved in ether and washed repeatedly with water and dried over magnesium sulfate to give the free base which is treated with fumaric acid and recrystallized from butanone to give 3,6-bis(4-dimethylaminobutyryl)-N-ethylcarbazole bis acid fumarate. M.P. 94°–98°C.

EXAMPLE 33

3,6-Bis(5-diethylaminovaleryl)-N-methylcarbazole

Following the procedure of Example 32, only substituting respectively for 3,6-bis(4-chlorobutyryl)-N-ethylcarbazole and dimethylamine the appropriate molar equivalent amount of 3,6-bis(5-chlorovaleryl)-N-methylcarbazole, prepared from N-methylcarbazole and 5-chlorovaleryl chloride, and an excess of diethylamine, 3,6-bis(5-diethylaminovaleryl)-N-methylcarbazole is obtained.

EXAMPLE 34

2,6-Bis(4-diethylaminobutyryl)-N-methylcarbazole

To a solution of 2.5 equivalents of 3-diethylaminopropylmagnesium chloride and 3-diethylaminopropylchloride in tetrahydrofuran, is added dropwise a solution of 1 equivalent of 2,6-dicyano-N-methylcarbazole, which is prepared by treatment with dimethylsulfate in the presence of sodium hydroxide and subsequent dehydrating the diamide by heating with phosphorous pentoxide, in tetrahydrofuran. When the addition is complete the reaction mixture is gently refluxed for 2 hours, then stirred at room temperature for several hours. The resulting complex is decomposed by treatment with saturated ammonium chloride, and the organic material is extracted with chloroform. The chloroform layer is treated with dilute HCl with warming. The aqueous solution is filtered, made alkaline and extracted with ether. The ether extract is dried over magnesium sulfate and evaporated to dryness to give 2,6-bis(4-diethylaminobutyryl)-N-methylcarbazole.

EXAMPLE 35

3,6-Bis(4-aminobutyryl)carbazole dihydrochloride

An ethanolic solution of 1 equivalent of 3,6-bis-(4-chlorobutyryl)carbazole, prepared from carbazole and 4-chlorobutyryl chloride, and 2.4 equivalents of hexamethylenetetramine are reacted at reflux for 36 hours. The solution is acidified with 3N HCl, digested for several hours and the solvent removed under reduced pressure to give the desired product which is recrystallized from methanol-ethyl acetate.

EXAMPLE 36

3,6-Bis(dimethylaminoacetyl)-N-ethylcarbazole dihydrochloride dihydrate

A mixture of 14.6 g (0.042 mole) of 3,6-bis(-chloroacetyl)-N-ethylcarbazole, prepared from N-ethylcarbazole and chloroacetyl chloride, 100 ml of 40% dimethylamine and 7.0 g of potassium iodide in 200 ml of butanone is placed in a Parr bomb and heated at 70°–80°C with stirring for 2 hours. The reaction mixture is cooled and poured into 2.0 l of ice water. The solid which precipitates is filtered off, dissolved in chloroform and dried over magnesium sulfate to give the free base of the desired product which is subsequently converted to the dihydrochloride salt and recrystallized from methanol-acetone to give the desired product.

EXAMPLE 37

An illustrative composition for tablets is as follows:

| | | Per Tablet |
|---|---|---|
| (a) | 2,7-bis(2-diethylaminoethoxy)-fluoren-9-one dihydrochloride | 100.0 mg |
| (b) | wheat starch | 15.0 mg |
| (c) | lactose | 33.5 mg |
| (d) | magnesium stearate | 1.5 mg |

A portion of the hweat starch is used to make a granulated starch paste which together with the remainder of the wheat starch and the lactose is granulated, screened and mixed with the active ingredient, that is, (a), and the magnesium stearate. The mixture is compressed into tablets weighing 150 mg each.

EXAMPLE 38

An illustrative composition for a parenteral injection is the following wherein the quantities are on a weight to volume bases.

| | | Amount |
|---|---|---|
| (a) | N-ethyl-3,6-bis(2-diethylaminoethoxy)carbazole dihydrochloride | 100.0 mg |
| (b) | sodium chloride | q.s. |
| (c) | water for injection to make | 10.0 ml |

The composition is prepared by dissolving the active ingredient, that is (a), and sufficient sodium chloride in water for injection to render the solution isotonic. The composition may be dispensed in a single ampule containing 100 mg of the active ingredient for multiple dosage or in 10 ampules for single dosage.

EXAMPLE 39

An illustrative composition for hard gelatin capsules is as follows:

| | | Per Capsule |
|---|---|---|
| (a) | 2,6-bis(2-diisopropylaminoethoxy)-anthraquinone dihydrochloride | 200.0 mg |
| (b) | talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 40

An illustrative composition for pills is as follows:

| | | Per Pill |
|---|---|---|
| (a) | 3,9-bis(2-dimethylaminoacetyl)-fluoranthene dihydrochloride | 200 mg |
| (b) | corn starch | 130 mg |
| (c) | liquid glucose | 20 ml |

The pills are prepared by blending the active ingredient (a) and the corn starch then adding the liquid glucose with thorough kneading to form a plastic mass from which the pills are cut and formed.

I claim:

1. A method of treating conditions of delayed hypersensitivity which comprises administering to a patient in need thereof a compound selected from the formula

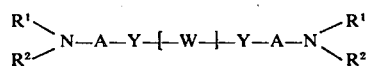

wherein [W] is an aromatic polycyclic nucleus selected from fluoranthene, fluorene, fluoren-9-ol, fluoren-9-one, or anthraquinone; Y is selected from carbonyl, divalent sulfur, or oxygen with the proviso that when Y is carbonyl, [W] is other than fluoren-9-ol or anthraquinone; A is selected from a straight or branched alkylene chain of from 1 to 6 carbon atoms; and each of $R^1$ and $R^2$ is selected from hydrogen, straight or branched lower alkyl of from 1 to 4 carbon atoms, or alkenyl of 3 to 6 carbon atoms, having the vinyl unsaturation in other than the 1-position; and pharmaceutically acceptable acid addition salts thereof, in an amount effective to suppress delayed hypersensitivity.

2. A method of claim 1 wherein Y is oxygen.

3. A method of claim 2 wherein [W] is fluoren-9-one.

4. A method of claim 3 wherein the compound is 2,7-bis(2-diethylaminoethoxy)fluoren-9-one or a pharmaceutically acceptable acid addition salt thereof.

5. A method of claim 2 wherein [W] is fluoranthene.

6. A method of claim 5 wherein the compound is 3,9-bis(3-diethylaminopropoxy)fluoranthene or a pharmaceutically acceptable acid addition salt thereof.

7. A method of claim 2 wherein [W] is anthraquinone.

8. A method of claim 7 wherein the compound is 2,6-bis(2-dimethylaminoethoxy)anthraquinone or a pharmaceutically acceptable acid addition salt thereof.

9. A method of claim 1 wherein Y is carbonyl.

10. A method of claim 9 wherein [W] is fluorene.

11. A method of claim 10 wherein the compound is 2,7-bis(2-diethylaminoacetyl)fluorene or a pharmaceutically acceptable acid addition salt thereof.

12. A method of claim 9 wherein [W] is fluoranthene.

13. A method of claim 12 wherein the compound is 3,9-bis(2-dimethylaminoacetyl)fluoranthene or a pharmaceutically acceptable acid addition salt thereof.

* * * * *